United States Patent
Rosado Loria et al.

(10) Patent No.: US 8,324,185 B2
(45) Date of Patent: Dec. 4, 2012

(54) COMPOSITION FOR THE TREATMENT OF OBESITY AND HYPERLIPIDEMIA

(75) Inventors: Jorge Luis Rosado Loria, Queretaro (MX); Miguel Angel Duarte Vàzquez, Guanajuato (MX); Sandra García Padilla, Queretaro (MX)

(73) Assignee: Nucitec, S.A. DF C.V., Queretaro, Queretaro (MX)

( * ) Notice: Subject to any disclaimer, the term of this patent is extended or adjusted under 35 U.S.C. 154(b) by 636 days.

(21) Appl. No.: 11/718,046

(22) PCT Filed: Jul. 18, 2005

(86) PCT No.: PCT/MX2005/000058
§ 371 (c)(1),
(2), (4) Date: Apr. 20, 2009

(87) PCT Pub. No.: WO2006/046847
PCT Pub. Date: May 4, 2006

(65) Prior Publication Data
US 2009/0197831 A1 Aug. 6, 2009

(30) Foreign Application Priority Data
Oct. 28, 2004 (MX) .................... PA/a/2004/010692

(51) Int. Cl.
*A01N 43/04* (2006.01)

(52) U.S. Cl. .............................. 514/55; 514/23; 514/54
(58) Field of Classification Search .................. None
See application file for complete search history.

(56) References Cited

U.S. PATENT DOCUMENTS
6,030,953 A * 2/2000 Bailly et al. ................... 514/25

OTHER PUBLICATIONS
Shenoy et al. Biomacromolecules (2003), vol. 4, pp. 265-272.*

* cited by examiner

*Primary Examiner* — Patrick Lewis
(74) *Attorney, Agent, or Firm* — Sterne, Kessler, Goldstein & Fox P.L.L.C.

(57) ABSTRACT

Current invention is related to the pharmaceutical industry in general and to the industry of the manufacture of pharmaceutical products for weight reduction and hyperlipidemia treatment. The advantages of the current invention respect of the similar of the state of the art are that in the present invention side effects normally produced by the consumption of lipase inhibitors are eliminated; optimizing both the lipase inhibitor component and the fat-trapping; with the adequate composition of each one of the components and with very small amounts of each one. The invention consists of a composition for the treatment of the obesity and hyperlipidemia, characterized by comprising in combination a lipase inhibitor and a fat-trapping component.

6 Claims, No Drawings

COMPOSITION FOR THE TREATMENT OF OBESITY AND HYPERLIPIDEMIA

CROSS REFERENCE TO PRIOR APPLICATIONS

This application claims the benefit of PCT International Application No. PCT/MX2005/000058, filed Jul. 18, 2005, which claims priority from Mexican Patent Application No. PA/a/2004/0010692, filed Oct. 28, 2004, the entire disclosures of which are incorporated by reference herein.

FIELD OF THE INVENTION

The present invention is related to the pharmaceutical industry in general and to the industry of the manufacture of pharmaceutical products for obesity, weight reduction and hiperlipidemia treatment.

BACKGROUND OF THE INVENTION

Obesity is a chronic disease and as such it needs for a long-term treatment. Obesity is essentially the consequence of a long term positive energy balance. Positive energy balance occurs when energy intake is higher than energy expenditure. In particular, excessive fat intake plays a very important role in the development of obesity.

The main therapy that needs to be considered initially to treat obesity is an improvement in dietary habits of the patient and increasing physical activity or exercise. Nevertheless, when the problem of obesity is not solved by this strategy or it is associated with other disorders, pharmacological treatment is required. Most of drugs used for the treatment of obesity operate diminishing fat consumption by a mechanism of suppression food intake, these drugs act at a level of the Central Nervous System and have an anorexigenic effect, (i.e they reduce hunger) thus they cannot be used for a long-term treatment.

Obesity being a disease that may unleash many other diseases including diabetes, hypertension and atherosclerosis, a huge amount of research has been developed to obtain biomolecules that help to solve the problem. Recently, inhibitors of the lipase enzyme are the molecules most used with this purpose.

This type of drugs diminish fat absorption by inhibiting the activity of pancreatic lipase enzyme avoiding fat hydrolysis into their most singles components, promoting their elimination without being absorbed.

Lipase enzymes hydrolyze ester bonds from lipids, releasing fatty acids and glycerol. In Human beings triglycerides digestion is carried out mainly by the action of three enzymes: gastric lipase, carboxyl ester lipase and pancreatic lipase. Released fatty acids are incorporated into phospholipids micelles and eventually get into blood stream as chylomicrons.

Lypase is a water-soluble enzyme, contrasting with its substrates which are water-insoluble. Thus, substrates must be emulsified with bile salts to allow their hydrolysis by lipase enzyme. In fact lipases are only active in the inter-phase oil:water, suffering an irreversible denaturalization or conformational changes required for the linkage with the substrate, producing an activated complex that later derivates in the product.

The most used lipase inhibitor is orlistat or tetrahidrolipstatin. This has a low efficiency, since only diminish fat absorption from the diet by 30%. This low efficiency is due to its mechanism of action since being a competitive inhibitor it needs to act directly in the active place of the enzyme, which is complicated by the complex system formed during the fat digestion process.

Although in vitro orlistat fully inhibits pancreatic lipase activity, its efficacy in vivo is affected mainly by the system on which fat digestion takes place, characterized by discontinuous system of oil emulsified in water.

U.S. Pat. No. 4,598,089 describes the use of lipstatin and tetrahydrolipstatin for the prevention and treatment of obesity and hyperlipidemy. Lipstatin and tetrahydrolipstatin are powerful inhibitors of gastric and pancreatic lipase, with their use it has been demonstrated a reduction in fat absorption of up to 30% of dietary fat.

These molecules inhibit lipase in a competitive and irreversible manner, to carry out the inhibitory function they require to be in contact with the active site of the enzyme, which could be complicated by the complex system formed during fat digestion. Lipstatin is normally used at a dose of 120 mg per meal, an increment in dosing does not increase efficacy, but does increase the experience of adverse effects.

Gargouri et al (Gargouri et al., "Studies on the inhibition of pancreatic and microbial lipases by soybean proteins"; J Lipid Res., 25: 1214-1221 1984) reported that some proteins such as serum albumin, β-lactoglobulin, and certain soybean proteins inhibit some lipases activity. These molecules do not act directly on the enzyme, but they modify the lipid emulsion, avoiding the contact of the enzyme with the substrate.

Wang y Huang (Wang y Huang "Inhibitors of lipase activities in soybean and other oil seeds"; Plant Physiol., 76: 929-934 1984), Tani et al (Tani et al., "Purification and characterization of proteinous inhibitor of lipase from wheat flour"; J Agric Food Chem., 42:2382-2385 1994) early reported the presence in some grains of basic proteins with inhibitory lipase activity, and later Miyazaki et al in the US patent (U.S. Pat. No. 5,411,9569) described some basic proteins that could be used as lipase inhibitors for obesity treatment.

One of the main side effects observed when lipase inhibitors are used for obesity treatment is the sudden oily anal leakage, which happens as a result of the physical separation of the not absorbed liquid fat from the fecal matter in the intestine. Several inventions have been developed with the purpose of prevent this effect.

Some patents have suggested a combination of the lipase inhibitor with insoluble fibers to significantly reduce side effects. The problem with this approach is the adequate selection of a polymer or fiber.

Smidt et al. In the U.S. Pat. No. 6,703,369 describe the invention of a chewable product containing soluble fiber, preferably methyl-cellulose and a lipstatine derivative, preferably orlistat. Cellulose addition helps to control undesirable side effects of lipstatine consumption as lipase inhibitor.

Josefiak in the U.S. Pat. No. 6,726,906 disclosed a method to treat obesity and high triglycerides concentration in blood by means of a reduction of fat absorption. This method comprised oral administration of a fat trapping polymer in combination with a lipase inhibitor lipstatin or tetrahidrolipstatin, claiming that the fat trapping polymer helps to eliminate typical adverse side effects such as steatorrhea and other gastrointestinal problems that occur with the administration of lipase inhibitors.

Polyacrilamide as such is non-toxic, however, after polymerization, this polymer can have non-polymerize residues which could be in the range of 0.05% to 5.0% of the final product. It is known that non-polymerized acrilamide residues are highly neurotoxic and highly water soluble and can be absorbed by any exposure route such as respiratory or digestive or even by dermal exposure. (Windholz, Merck Index 10th ed. 1989; Croll et al., "Residues of acrylamide in water"; Water Res., 8,989-993 1974.

Other document patents disclosed the use of insoluble fiber with this purpose (Smidt et al., U.S. Pat. No. 6,703,369; Hug et alt., Niazi U.S. Pat. No. 6,251,421), in these cases the action of the fibers is more physical and mechanical than chemical and therefore a huge amount is required to carry out an adequate function.

Other patents suggest the use of gums acting as fat-trapping polymers such as xantana gum (Hug et al., U.S. Pat. No. 6,358,522) and konjac (Bailly U.S. Pat. No. 6,030,953) however, these compounds can act also as emulsifiers and as such they create proper conditions for lipase activity promoting fat absorption.

Bailly et al (U.S. Pat. No. 6,030,953) developed an invention for the treatment of obesity. Particularly, this invention is composed of lipase inhibitor (orlistat or tetrahidrolipstatina) and konjac or glucomanan. The use of konjac or glucomanan prevents the gastrointestinal problems produced by the lipase inhibitor of lipasa that have been already discussed.

Hug et al (U.S. Pat. No. 6,358,522) based on remarks of the U.S. Pat. No. 5,447,953, in which it was demonstrated that the combination of lipase inhibitors with insoluble fiber, make it possible to diminish fat absorption higher than that observed by the administration of the inhibitor alone; developed a pharmaceutical composition which comprises the administration of a lipase inhibitor (orlistat) together with a food grade hydrocolloid with the purpose of diminishing the adverse effects of the lipase inhibitor. Such hydrocolloid was selected from the group of natural or semi-synthetic polysaccharides such as metylcellulose, xantana gum, Psyllium plantago or combination of them.

The sheath of the Psyllium plant has been used in traditional medicine for more than 60 years. It is obtained from the seed or sheets of the Plantago ovata plant. In the United States it is used as laxative due to its absorbing water capability. It acts mainly through a mechanical effect trapping the colonic content reducing intestinal transit time. Niazi (U.S. Pat. No. 6,251,421) used the fiber of Psyllium in combination with a lipase inhibitor (orlistat) in a pharmaceutical composition to diminish fat absorption. The pharmaceutical composition reduces the absorption of fat through the inhibition of gastrointestinal lipase.

The main disadvantage of all preparations containing soluble fiber is related to the huge amount of fiber that has to be supplied to produce the effect claimed in the patents (up to 10 g or more).

Also it has been proposed the use of gums as xantan gum and konjac gum, nevertheless, these gums have a recognized capacity as emulsifier and create a proper environment for the function of lipasa, as it has been documented by (Tsujita et to., "Studies on the inhibition of pancreatic carboxilester lipase by protamine"; J Lipid Animal., 37: 1481-1487 1996).

There exist other preparations that have suggested the use of crystalline cellulose and metyl-cellulose, nevertheless their fat-trapping effect is lower as compared with those of the polymer suggested here (Bailly et to., U.S. Pat. No. 6,030, 953).

OBJECTIVES OF THE INVENTION

The main objective of the current invention is to make possible a pharmaceutical composition for the treatment of the obesity and hyperlipidemia formed by a lipase inhibitor and a fat-trapping compound, in which there are eliminated the side effects normally produced by the consumption of a lipase inhibitor.

Other objective of the present invention is to achieve the previous advantage optimizing both, the lipase inhibiting component, and the fat-trapping component.

Even other another objective is to make possible the previous objective with the suitable concentration of each component.

Even more another objective is to obtain the previous composition requiring very small quantities of each component so that the composition is effective without producing side undesired effect.

Other objectives of the current invention will be clear from the study in the following description.

BRIEF DESCRIPTION OF THE INVENTION

The present invention consists of a useful composition for the treatment of the obesity and hyperlipidemia, comprising a combination of a specific lipase inhibitor and a specific fat-trapping.

The lipase inhibitor is a basic peptide (polylisine) formed by the linkage by means of peptide bond of several monomers of the amino acid lisine, in which the amino group amino has a pK value close to 9 and the R group close to 101 in such a way that at biological pH, this amino acid is charges positively. Due to the great number of positive charges it has the capability to alter the balance of bile salts and fats, eventually destroying the emulsion.

It has been reported that the peptide polylisine used in our preparation, retains its inhibitory activity over fat absorption in the human body for a long time, which gives as a result a major reduction of fat absorption (Miyazaki et al., U.S. Pat. No. 5,411,956).

Another lipase inhibitor of with the same characteristics that can be used in this preparation is the protamine. Protamine is 5000 kDa molecular weight polypeptide formed mainly by the amino acids lisine and arginine, whose confer a clear positive net charge making possible its interaction with the emulsified substrate breaking-down the emulsion and in this way inhibiting lipase activity.

In this preparation the lipase inhibitor is combined with a fat-trapping polymer with a double purpose: to increase the efficiency in the inhibition of fat absorption and to eliminate the side problems associated with the consumption of lipase inhibitors.

The increase of the inhibitory effect of fat absorption is achieved by the increase of rate of the intestinal transit of the food produced by the insoluble compound. The polymer also will trap the fat released from the breakage of the emulsion produced by the use of lipase inhibitors, eliminating oily anal leakage.

The trapping-fat polymer used is the Chitosano. Chitosan is a polysaccharide type biopolymer non-digestible, poly-N-acetilglucosamine, that forms aggregates at intestinal level with cholesterol and fatty acids, diminishing their absorption and favoring their fecal elimination.

For a better comprehension of the invention, we will show a detailed description of some modalities of the same one.

DETAILED DESCRIPTION OF THE INVENTION

The composition of polilisina or protamina as lipase inhibitors plus chitosan motive of the present invention reduces the absorption of fat coming from the diet by means of the inhibition of the gastrointestinal lipase.

The pharmaceutical composition of the present invention reduces the absorption of fat coming from the diet through the inhibition of the gastrointestinal lipase enzyme. The used inhibitors are polylisine and/or protamina, both molecules are positively charged and they have the capability to interact with the emulsified substrate to prevent the absorption of the enzyme in the interface, thus inhibiting its activity.

The combination of the lipase inhibitor of with the fat-trapping polymer (chitosan), increases the inhibitory effect on fat absorption, such synergic effect is attributable to the rate increase of the gastrointestinal transit of the food produced by the insoluble polymer.

Additionally, the use of a fat-trapping polymer is useful for the treatment and prevention of some of the adverse effects that are observed as consequence of the administration of inhibiting of lipase, or after the consumption of meals that contain not absorbable or poorly absorbable fat or fat substitutes.

The present invention is also related to the use of the lipase inhibitor (polylisina or protamina) combined with small quantities of chitosan, for the treatment of obesity and hyperlipidemia.

The characteristics of the inhibiting peptides of lipase motive of this invention, offers a valuable option to diminish fat absorption. The mechanism is due to his big number of positive charges that provokes a breakage of the emulsion of the fat reducing the action of the gastric lipasa.

The characteristics of the peptides inhibiting lipase motive of this invention, turn the peptides on a valuable option to diminish fat absorption, due to their great number of positive charges it provokes a break-down of the fat emulsion, reducing the action of the gastric lipase.

Tests in our laboratory have demonstrated that polylisine and protamine at concentrations as low as 10 µg/mL produce a break-down of up to 90% of the emulsion.

One of the initial problems to solve, was to find the best system to determine lipase activity, since the fat must be emulsified and the enzyme come into the water:oil interphase to carry out the conformational modification that allows a proper orientation and therefore a better function of the lipase, besides the system must be similar to the one that is formed during fat digestion in the organism, which are emulsified by bile salts.

The final system selected was that formed by olive oil, as substrate, calcium acetate, phosphatidilcholine and colic acid, being the last two the components presents in a predominant proportion in bile salts. This is particularly important since although there exist other compounds that can work as emulsifiers such as gums, in these systems the peptides used are not capable of breaking-down the emulsion.

Being of a protein nature, the peptides motive of this invention could be degraded by the proteases present in the digestive tract, such as trypsin and pepsin, in addition to the pH conditions existing in the gastrointestinal tract. Several peptides and basic proteins were proved as for their stability against digestion, those peptides that were chosen are those of major stability.

The invention has been sufficiently described so that a person with average knowledge in the matter could reproduce and obtain the results that we mention in the present invention.

Nevertheless, any skilful person in the field that encompasses the present invention can be capable of making modifications not described in the present request, nevertheless, if for the application of these modifications in a certain structure or in the manufacture process of the same one, the compounds claimed in the following claims are required, the above mentioned structures will have to be include within the scope of the invention.

Having described sufficiently the invention, it is considered to be an innovation and therefore the expressed and content is claimed as property in the following clauses claims:

1. A composition for the treatment of obesity and hyperlipidemia, comprising in combination a lipase inhibitor and a fat-trapping compound in amounts effective to treat obesity and hyperlipidemia, wherein the lipase inhibitor is selected from the group comprising polylisine, protamine or combinations thereof and wherein the fat-trapping compound is a chitosan.

2. The composition for the treatment of the obesity and hyperlipidemia according to claim 1, wherein the protamine comprises protamine sulfate.

3. The Composition for the treatment of obesity and hyperlipidemia according to claim 2, wherein the chitosan is present in quantities of 300 mg to 20 g, and wherein the lipase inhibitor is present in quantities ranging from 10 mg to 5000 mg.

4. The composition for the treatment of obesity and hyperlipidemia according to in claim 1, wherein the composition is in the form selected from the group consisting of capsules, tablets and liquid formulations.

5. The composition for the treatment of obesity and hyperlipidemia according to in claim 2 wherein the form of the composition is selected from the group consisting of capsules, tablets and liquid formulations.

6. The composition for the treatment of obesity and hyperlipidemia according to in claim 3 wherein the form of the composition is selected from the group consisting of capsules, tablets and liquid formulations.

* * * * *